US008680154B2

(12) United States Patent
Barbot

(10) Patent No.: US 8,680,154 B2
(45) Date of Patent: Mar. 25, 2014

(54) INJECTABLE VETERINARY COMPOSITION

(75) Inventor: Carole Barbot, Boos (FR)

(73) Assignee: Intervet International B.V., Boxmeer (NE)

( * ) Notice: Subject to any disclaimer, the term of this patent is extended or adjusted under 35 U.S.C. 154(b) by 1460 days.

(21) Appl. No.: 11/722,280

(22) PCT Filed: Dec. 20, 2005

(86) PCT No.: PCT/EP2005/056950
§ 371 (c)(1),
(2), (4) Date: Jun. 20, 2007

(87) PCT Pub. No.: WO2006/067138
PCT Pub. Date: Jun. 29, 2006

(65) Prior Publication Data
US 2009/0275662 A1 Nov. 5, 2009

Related U.S. Application Data

(60) Provisional application No. 60/638,154, filed on Dec. 21, 2004.

(30) Foreign Application Priority Data

Dec. 21, 2004 (EP) .................... 04106809

(51) Int. Cl.
*A61K 47/10* (2006.01)
*A61K 47/22* (2006.01)

(52) U.S. Cl.
USPC ........... 514/628; 514/424; 514/618; 514/947; 424/400

(58) Field of Classification Search
USPC .................. 514/628, 424, 618, 947; 424/400
See application file for complete search history.

(56) References Cited

U.S. PATENT DOCUMENTS

| 4,235,892 A | 11/1980 | Nagabhushan |
| 4,311,857 A | 1/1982 | Nagabhushan |
| 4,582,918 A | 4/1986 | Nagabhushan et al. |
| 4,743,700 A | 5/1988 | Jommi et al. |
| 4,876,352 A | 10/1989 | Schumacher et al. |
| 4,912,138 A | 3/1990 | Pozzi et al. |
| 4,973,750 A | 11/1990 | Nagabhushan et al. |
| 5,105,009 A | 4/1992 | Jommi et al. |
| 5,227,494 A | 7/1993 | Schumacher et al. |
| 5,352,832 A | 10/1994 | Wu et al. |
| 5,382,673 A | 1/1995 | Clark et al. |
| 5,567,844 A | 10/1996 | Jommi et al. |
| 5,663,361 A | 9/1997 | Towson et al. |
| 2003/0220302 A1 | 11/2003 | Kohan et al. |
| 2004/0242546 A1 | 12/2004 | Freehauf et al. |

FOREIGN PATENT DOCUMENTS

| EP | 0621033 | 4/1993 |
| EP | 0546018 | 10/1994 |
| GB | 2000970 | 1/1979 |
| WO | WO9204016 | 3/1992 |
| WO | WO2004014340 | 2/2004 |

OTHER PUBLICATIONS

Handbook of Pharmaceutical Excipients, published by American Pharmaceutical Association/The Pharmaceutical Society of Great Britain, 1986, p. 127.
Fiedler, Herbert P., Lexikon der Hilfsstoffe fur Pharmazie, Kosmetik and angrenzende Gebiete, 3rd edition, 1989, p. 577. This paper is not in English. See second full paragraph of p. 4 of Applicant's specification for a discussion relating to this reference.
Schafer, Thomas W. et al., Novel Fluorine-Containing Analogs of Chloramphenicol and Thiamphenicol: Antibacterial and Biological Properties, in Current Chemotherapy and Infectious Disease Proceedings of the 11th ICC and the 19th ICAA American Society of Microbiology, 1980 pp. 444-446.

*Primary Examiner* — Savitha Rao

(57) ABSTRACT

Injectable veterinary composition comprising a fluorinated chloramphenicol or thiamphenicol derivative and a solvent system comprising an ether of 1,2-ethanediol oligo- or polymers, and a pyrrolidone solvent.

9 Claims, 1 Drawing Sheet

Plasma concentration µg/ml of Florfenicol-

Individual concentration-time curves (Formulation A)

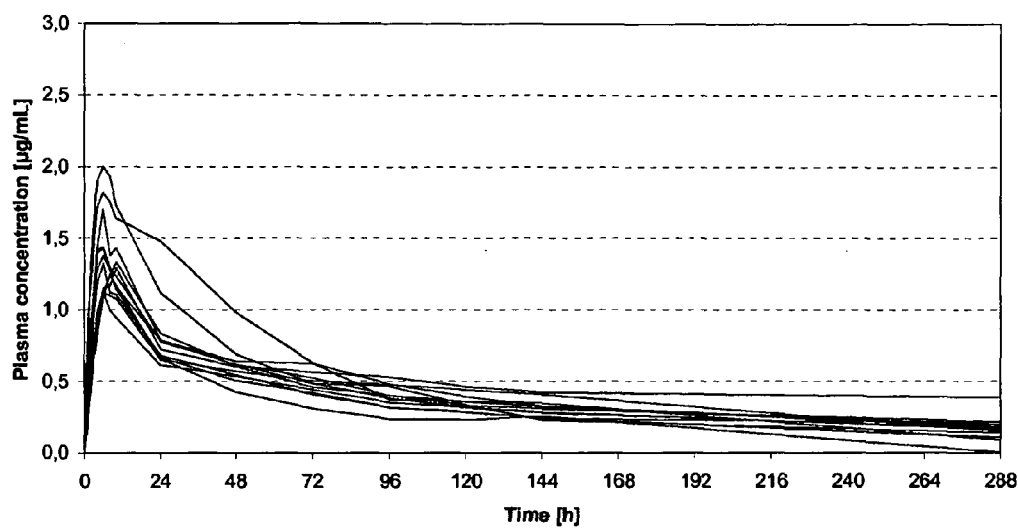
Plasma concentration µg/ml of Florfenicol-
Individual concentration-time curves (Formulation A)

INJECTABLE VETERINARY COMPOSITION

PRIORITY CLAIM TO RELATED PATENT APPLICATIONS

This patent claims priority under 35 U.S.C. §371 as a national phase of International Patent Application No. PCT/EP2005/056950 (filed Dec. 20, 2005; and published on Jun. 29, 2006 as International Publication No. WO 2006/067138), which, in turn, claims priority to U.S. Provisional Patent Application No. 60/638,154 (filed Dec. 21, 2004), and European Patent Appl. No. 04106809.9 (filed Dec. 21, 2004). The entire text of each of the above-referenced patent applications is hereby incorporated by referenced into this patent.

FIELD OF THE INVENTION

The current invention relates to a composition for the treatment of microbial infection in an animal.

BACKGROUND OF THE INVENTION

Bovine respiratory disease (BRD) has been one of the leading causes of economic loss to both the dairy and beef industries throughout the world. Excessive mortality, reduced weight gains, and the cost of treatment and prevention have placed a heavy burden on the industry. For years, antimicrobial therapy has been the mainstay of BRD therapy. There are many effective antimicrobial agents currently available for the treatment of BRD e.g. Nuflor®, an injectable formulation of the broad-spectrum antibiotic florfenicol.

European patent No. 546018 discloses an injectable composition of florfenicol comprising 10 to 50% by weight of florfenicol; 10 to 65% by weight of a pyrrolidone solvent; 5 to 15% by weight of a viscosity reducing agent; and 5 to 40% by weight of polyethylene glycol. This formulation is however difficult to administer, especially under cold whether conditions because the viscosity of the formulation becomes too high causing this poor syringeability.

International patent application No. WO 92/04016 discloses a composition of florfenicol in a solvent system consisting essentially of aprotic polar solvents, e.g., N-methyl-2-pyrrolidone or 2-pyrrolidone.

International patent application No. WO 2004/014340 discloses a composition of 20% florfenicol in a solvent system comprising a mixture of a hydrophilic and a lipophilic solvent, e.g. laurocapram, a skin-penetration enhancer.

United States patent application No. US 2004/0242546 disclose compositions of florfenicol comprising triacetin, dimethylamide and/or combinations thereof as a carrier.

BRIEF SUMMARY OF THE INVENTION

It is an object of the present invention to provide alternative compositions with high concentration of florfenicol and related antibiotic compounds that can easily be loaded into and expelled from a syringe and provides after administration to an animal effective blood levels of the antibiotic compounds.

The present invention provides a composition for the treatment of microbial infection in an animal comprising an antibiotic compound selected from the group of chloramphenicol, thiamphenicol and florfenicol in a solvent system, characterized in that the solvent system comprises an aliphatic ether alcohol and a pyrrolidone solvent.

BRIEF DESCRIPTION OF THE FIGURE

FIG. 1 shows individual plasma concentration-time curves observed for Formulation A in units of µg/ml.

DETAILED DESCRIPTION OF PREFERRED EMBODIMENTS

The compositions of the present invention comprise at least one antibiotic compound selected from the group of chloramphenicol, thiamphenicol and florfenicol.

Fluorine-containing analogs of antibiotics chloramphenicol and thiamphenicol have been shown to have antibiotic activity, both against organisms sensitive to and resistant to chloramphenicol and thiamphenicol. See Schafer, T. W. et al., "Novel Fluorine-Containing Analogs of chloramphenicol and thiamphenicol: Antibacterial and Biological Properties," in CURRENT CHEMOTHERAPY AND INFECTIOUS DISEASE P ROCEEDINGS OF THE 11$^{TH}$ ICC AND THE 19$^{TH}$ ICM AMERICAN SOCIETY OF MICROBIOLOGY 1980, 444-446. Examples of such compounds, and methods for their manufacture, are described and claimed in U.S. Pat. No. 4,235,892. The medical profession has become increasingly concerned about the transference of bacterial resistance to humans when antibiotics useful in treating humans are administered to livestock. Because the chloramphenicol group of antibiotics is infrequently used now to treat humans, its derivatives are particularly appropriate for veterinary use. Of particular interest are the 3-fluoro, 3-deoxy derivatives.

A preferred antibiotic compound is florfenicol (D-(threo)-1-p-methylsulfonyl phenyl-2-dichloroacetamido-3-fluoro-1-propanol). Florfenicol is the active ingredient in the commercial product Nuflor®, that is marketed by Schering-Plough Animal Health. U.S. Pat. No. 4,235,892, describes the compound and a processes for making said compound. This patent is incorporated herein by reference.

Another preferred antibiotic compound is D-(threo)-1-p-methylsulfonyl phenyl-2-difluoroacetamido-3-fluoro-1-propanol, Processes for the manufacture of these preferred antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361. Another preferred antibiotic is thiamphenicol.

The concentration of florfenicol or other antibiotic compound typically is from 10% to 60% w/v; with the preferred level between 20% and 50% w/v. Especially preferred is a composition, comprising 30 to 45% w/v of florfenicol.

The solvent system in the composition according to the present invention comprises an aliphatic ether alcohol and a pyrrolidone solvent. The composition for the treatment of microbial infection in an animal comprises preferably in the solvent system 1 to 89% v/v of an aliphatic ether alcohol and 1 to 89% w/v of a pyrrolidone solvent.

Preferred in accordance with the present invention are compositions in which the aliphatic ether alcohol is an ether of 1,2-ethanediol oligo- or polymers. Especially preferred in accordance with the present invention are compositions in which the carrier is a terminal mono-ether of 1,2-ethanediol oligo- or polymers.

As carrier a pharmaceutically acceptable $C_{1-5}$ alkyl or tetrahydrofurfuryl di- or partial-ether of a low molecular weight mono- or poly-oxy-alkanediol is useful.

Suitable components are, e.g. di- or partial-, especially partial-, -ethers of mono- or poly-, especially mono- or di-, -oxy-alkanediols comprising from 2 to 12, especially 4 carbon atoms. Preferably the mono- or polyoxy-alkanediol moiety is straight-chained. Especially suitable for use in accordance with the invention are di- or partial-ethers of formula I $$R_1\text{-}[O\text{---}(CH_2)_2]_x\text{---}OR_2 \quad (I)$$

wherein
$R_1$ is $C_{1-5}$ alkyl or tetrahydrofurfuryl,
$R_2$ is hydrogen, $C_{1-5}$ alkyl or tetrahydrofurfuryl, and
x is an integer of from 1 to 6, especially from 1 to 4, most especially about 2.

Particularly preferred for use in accordance with the invention are partial ethers as defined above, e.g. products of formula I, wherein $R_2$ is hydrogen.

$C_{1-6}$ alkyl moieties in the above defined ethers may be branched or straight chain, e.g. including methyl, ethyl, n-propyl, i-propyl, n-butyl and t-butyl groups.

Such ethers are known products and commercially available or may be produced analogously to the known products. Especially preferred products of formula I for use in relation to the present invention are those known and commercially available under the trade name Transcutol.

Transcutol (CAS no. 31692-85-0) is the compound diethyleneglycol monoethyl ether of formula I, wherein $R_1\text{=}C_2H_5$, $R_2\text{=}H$ and x=2. Products for use in accordance with the present invention are those known and commercially available, e.g. under the trade name Transcutol® from Gattefosse, (St Priest, France), in particular the product Transcutol® P and HP.

Synonym names for transcutol are: 1-Hydroxy-3,6-dioxaoctane, 2-(2'-Ethoxyethoxy) ethanol, 2-(2-Ethoxyethoxy) ethanol, 2-(2-Ethoxyethyoxy) ethanol, 3,6-Dioxa-1-octanol, 3,6-Dioxa-1-oktanol, 3,6-Dioxaoctan-1-ol, Aethyldiaethylenglycol, APV, Carbitol, Carbitol cellosolve, Carbitol solvent, DEGEE, DEGMEE, Diethylene glycol ethyl ether, Diethylene glycol monoethyl ether, Diglycol monoethyl ether, Dioxitol, Dowanol, Dowanol 17, Dowanol DE, Ektasolve DE, Ethanol, 2,2'-oxybis-, monoethyl ether, Ethanol, 2-(2-ethoxyethoxy)-, Ether monoethylique du diethylene glycol, Ethoxy diglycol, Ethoxydiglycol, Ethyl carbitol, Ethyl diethylene glycol, Ethyl digol, Ethyldiethylene glycol, Ethyl carbitol Glycofurol (CAS No. 57-55-6), also known as tetrahydrofurfuryl alcohol polyethylene glycol ether or α-(tetrahydrofuranyl)-ω-hydroxypoly(oxy-1,2-ethanediyl) has the formula I wherein $R_1$=[CHEM-3]$R_2$=H and x has an average value of from 1 to 2. It has an average molecular weight of ca. 190; a b.p. of from ca. 80°-100. degree. C. (at 40N/m²), a density of ca. 1.070-1.090 g/cm³ (at 20° C.); a hydroxy value of ca. 300-400; a refractive index of ca. 1.4545 (sodium D line, 589 mm) (at 40° C.); and a viscosity of ca. 8-18 mN s/m² (at 200). (c.f. "Handbook of Pharmaceutical Excipients, published by American Pharmaceutical Association The Pharmaceutical Society of Great Britain (1986), p. 127 and Fiedler, "Lexikon der Hilfstoffe", 3rd edition (1989), p. 577.)

The precise properties of Glycofurol vary according to relative purity. Thus lower quality grades contain significant amounts of tetrahydrofurfuryl alcohol and other impurities.

Synonym names for gylcofurol are: Glycofurol 75; tetraglycol; Poly(oxy-1,2-ethanediyl), α-(tetrahydrofuranyl-ω-hydroxy-(9 Cl). Tetraglycol is also used as a synonym for tetrahydrofurfuryl alcohol.

The amount of aliphatic ether alcohol present in the compositions of the present invention is from 1 to 89% v/v, in one embodiment preferably from 15 to 25%, in another embodiment from 1 to 89% v/v, 20 to 50% v/v, 25 to 45% v/v and especially preferred 30 to 40% v/v.

Suitable pyrrolidone solvents for the composition according to the present invention are especially 2-pyrrolidone and N-methyl-2-pyrrolidone. The preferred solvent is N-methyl-2-pyrrolidone. Examples of compounds suitable for use in accordance with the present invention are those known and commercially available, e.g. under the trade name Pharmasolv® from International Specialty Products, (Wayne, N.J., U.S.A.). Particularly suitable is the product Polysolv® V.

The amount of pyrrolidone solvent in the compositions of the present invention may comprise from 1 to 89% w/v, preferably 20 to 50% w/v. Especially preferred are compositions, comprising 30% w/v to 40% of the pyrrolidone solvent.

The ratio between the amount of pyrrolidone solvent and the amount of florfenicol is between 0.6 and 1.1, especially preferred is a ratio between 0.7 and 0.9.

The composition according to the current invention may further comprise additional pharmaceutical excipients known in the art. Such pharmaceutical excipients are e.g. described in "Gennaro, Remington: The Science and Practice of Pharmacy", (20. Edition, 2000), incorporated by reference herein. Such ingredients include preservatives, chelating agents, antioxidants and stabilizers. Exemplary preservatives include methyl p-hydroxybenzoate (methylparaben) and propyl p-hydroxybenzoate (propylparaben). Exemplary chelating agents include edetate sodium. Exemplary antioxidants include butylated hydroxyanisole and sodium monothioglycerol.

The composition contemplated herein can, if desired, include more than one pharmacologically active ingredient.

In order to prepare the composition of the present invention, the vehicle(s) or a portion of the vehicle(s), are added to the compounding vessel, followed by the remaining excipients and the actives. The mixture is mixed until all solids are dissolved. Additional solvent to bring the composition to final volume may be added if needed. Additives, such as those listed above, may also be included in the vessel and mixed into the formulation (the order of addition is not critical).

The compositions of the present invention exhibit desirable properties which are useful characteristics for the administration of relatively high concentrations of florfenicol or other antibiotic compounds. The compositions are physically and chemically stable. The compositions have desirable viscosity characteristics which allows for good syringeability over a wide temperature range and ease of processing, such as good flow rate through sterilizing filter membranes.

By syringeable it is meant that the suspension can be withdrawn easily from an ampoule/vial into a syringe with a 16 to 18 gauge needle and subsequently injected from such a syringe through the 16 to 18 gauge needle intramuscularly (im) or subcutaneously (sc).

The composition according to the invention shows better syringeability than compositions currently available. The rheological properties and syringeability of prior art formulation and compositions according to the present invention are shown in Tables 1 and 2. Experiments 1 and 2 show the pharmacokinetic evaluation of compositions according to the invention after i.m. and s.c. administration to cattle.

The compositions according to the present invention are particularly useful for cattle and other bovids, swine, and other large mammals.

In addition to the treatment of bovine respiratory disease, the compositions of this invention are also suitable for the treatment of infectious diseases such as swine respiratory disease, footrot, acute mastitis, pinkeye (infectious keratoconjunctivitis), acute pneumonia, metritis and enteritis. The dosage regimen for treatment of such diseases would be as described above.

The compositions according to the present invention will generally be administered to cattle at 1 mg to 100 mg of the antibiotic compound(s) per kilogram of body weight. Preferably the compositions of the present invention will be administered to bovines at 20 mg to 50 mg of the antibiotic compound(s) per kilogram of body weight.

More preferably the dose will be 40 mg/kg of the antibiotic compound and is administered once subcutaneously. Also preferable is the administration of two doses of 20 mg/kg administered at time 0 and 48 hours post initial administration.

The compositions according to the present invention will generally be administered to swine at a dose of 15 mg to 100 mg of the antibiotic compound per kilogram of body weight. Preferably, the compositions of the present invention will be administered to swine at 20 mg to 50 mg of the antibiotic compound per kilogram of body weight.

The compositions may be administered once daily or divided into multiple doses. Often only one dose will be sufficient to treat the infection. In some circumstances, one dose followed by a second dose 48 hours later will be required to treat the animal.

An "effective amount" is the dose required to alleviate a particular symptom of an infection, infestation or disease or to protect an animal against infections, infestations or diseases. The precise dose will depend on the stage and severity of the infection, the susceptibility of the infecting organism to the composition, and the individual characteristics of the animal species being treated, as will be appreciated by one of ordinary skill in the art.

The following examples describe in detail the invention. Although certain presently preferred embodiments of the invention have been described herein, it will be apparent to those skilled in the art to which the invention pertains that variations and modifications of the described embodiments may be made without departing from the spirit and scope of the invention.

Example 1

An injectable solution (Formulation A) is prepared from the following:

| Ingredients | Weight/ml |
| --- | --- |
| Florfenicol | 45 g |
| N-methyl-2-pyrrolidone (NMP) | 30 g |
| Diethylene glycol monoethylether | ad 100 ml |

The solution is prepared according to the following procedure: N-methyl-2-pyrrolidone and diethylene glycol monoethylether are mixed well and then florfenicol is dissolved in the mixture and the clear solution is sterilized by filtration.

Example 2

An injectable solution (Formulation B) is prepared from the following:

| Ingredients | Weight/ml |
| --- | --- |
| Florfenicol | 45 g |
| N-methyl-2-pyrrolidone (NMP) | 30 g |
| Glycofurol | ad 100 ml |

The solution is prepared according to the following procedure: N-methyl-2-pyrrolidone and glycofurol are mixed well and then florfenicol is dissolved in the mixture and the clear solution is sterilized by filtration.

Example 3

An injectable solution (Formulation C) is prepared according to the process shown in Example 1:

| Ingredients | Weight/ml |
| --- | --- |
| Florfenicol | 40 g |
| N-methyl-2-pyrrolidone (NMP) | 30 g |
| Diethylene glycol monoethylether | ad 100 ml |

Example 4

An injectable solution (Formulation D) is prepared according to the process shown in Example 2:

| Ingredients | Weight/ml |
| --- | --- |
| Florfenicol | 40 g |
| N-methyl-2-pyrrolidone (NMP) | 30 g |
| Glycofurol | ad 100 ml |

Example 5

An injectable solution (Formulation E) is prepared according to the process shown in Example 2:

| Ingredients | Weight/ml |
| --- | --- |
| Florfenicol | 45 g |
| N-methyl-2-pyrrolidone (NMP) | 37 g |
| Glycofurol | ad 100 ml |

Example 6

An injectable solution (Formulation F) is prepared according to the process shown in Example 1:

| Ingredients | Weight/ml |
| --- | --- |
| Florfenicol | 30 g |
| N-methyl-2-pyrrolidone (NMP) | 30 g |
| Diethylene glycol monoethylether | ad 100 ml |

Example 7

An injectable solution (Formulation G) is prepared according to the process shown in Example 1:

| Ingredients | Weight/ml |
|---|---|
| Florfenicol | 45 g |
| N-methyl-2-pyrrolidone (NMP) | 35 g |
| Diethylene glycol monoethylether | ad 100 ml |

TABLE 1a

Comparison of rheological profile of florfenicol compositions under various temperature conditions

| Composition | Formulation A | Formulation B | Reference prior art formulation |
|---|---|---|---|
| Florfenicol (g) | 45 | 45 | 30 |
| NMP (g) | 30 | 30 | 25 |
| Propylene glycol | | | 15 |
| Macrogol 300 | | | ad 100 ml |
| Glycofurol | | ad 100 ml | |
| Transcutol | ad 100 ml | | |
| Specific gravity | 1.157 | 1.196 | 1.167 |
| Rheological profile at room temperature | | | |
| viscosity (Pa · s) | 0.043 | 0.089 | 0.11 |
| yield point (Pa) after 5° C. storage | −0.12 | 0.051 | 0.215 |
| viscosity (Pa · s) | 0.032 | 0.31 | 0.57 |
| yield point (Pa) after −18° C. storage | 1.01 | 0.96 | 0.96 |
| viscosity (Pa · s) | 0.20 | 0.47 | 0.47 |
| yield point (Pa) | 0.9 | 0.89 | 0.91 |

TABLE 1b

Syringeability of florfenicol compositions under various temperature conditions

| Composition | Formulation A | Formulation B | Reference prior art formulation |
|---|---|---|---|
| Syringeability (1.5 mm) at room temperature | | | |
| suction time (sec) | 7.3 | 11.6 | 14.0 |
| emptying time (sec) after 5° C. storage | 3.3 | 4.0 | 5.6 |
| suction time (sec) | 12.3 | 18.3 | 20.3 |
| emptying time (sec) after −18° C. storage | 3.3 | 4.3 | 5.3 |
| suction time (sec) | 9.0 | 15.3 | 19.6 |
| emptying time (sec) | 3.3 | 4.3 | 5.0 |

TABLE 2

Comparison of rheological profile and syringeability of florfenicol compositions

| Composition | Formulation C | Formulation D | Reference prior art formulation |
|---|---|---|---|
| Florfenicol (g) | 40 | 40 | 30 |
| NMP (g) | 30 | 30 | 25 |
| Propylene glycol | | | 15 |
| Macrogol 300 | | | ad 100 ml |
| Glycofurol | | ad 100 ml | |
| Transcutol | ad 100 ml | | |
| Specific gravity | 1.14 | 1.181 | 1.167 |
| Rheological profile at room temperature | | | |
| viscosity (Pa · s) | 0.0094 | 0.013 | 0.11 |
| yield point (Pa) | 1.1 | 1.08 | 0.215 |
| Syringeability (1.5 mm) at room temperature | | | |
| suction time (sec) | 6.3 | 9.3 | 14.0 |
| emptying time (sec) | 2.6 | 4.3 | 5.6 |

Experiment 1

Formulations A and B and the reference prior art formulation were administered subcutaneously at a dose of 40 mg/kg florfenicol to cattle of 206 to 279 kg BW.

Formulation A was tested in a cross over design (6 animals treated with Formulation A followed by reference prior art formulation 29 days later and 6 animals treated vice versa). The pharmacokinetic profile of B was investigated in a single treatment design (n=6). Florfenicol concentrations in plasma samples taken prior to and 1, 2, 4, 6, 8, 10, 24, 48, 72, 96, 120, 144 and 288 hours following each treatment were determined by HPLC and pharmacokinetic parameters were calculated:

TABLE 3

Summary of pharmacokinetic parameters

| Test item | n | T max [h] | C max [µg/mL] | AUC [h*µg/mL] |
|---|---|---|---|---|
| Formulation A | 12 | 6.83 | 1.43 | 116.63 |
| Formulation B | 6 | 6 | 1.61 | 122.07 |
| Reference prior art formulation | 12 | 6.67 | 2.12 | 127.77 |

Experiment 2

In Experiment 2 pharmacokinetic parameters of the Formulations A E and F were evaluated compared to a reference prior art formulation Groups of 6 cattle (3 heifers and 3 bulls) of 186-241 kg bodyweight (BW) were treated either subcutaneously at dose of 1×40 mg florfenicol/kg BW or intramuscularly at a dose of 2×20 mg florfenicol/kg BW at a 48 hour interval.

Florfenicol concentrations in plasma samples taken prior to and 1, 2, 4, 6, 8, 10, 24, 48, 72, 96, 120, 144 and 288 hours following each treatment were determined by HPLC and pharmacokinetic parameters were calculated:

TABLE 4

Mean values of pharmacokinetic parameters after treatment with Formulations A, E and F compared to a reference prior art formulation

| Treatment (n = 6) | Tmax [h] | Cmax [μg/mL] | AUC (0-LOQ) [μg/mL*h] |
|---|---|---|---|
| Subcutaneous treatment at a dose of 40 mg florfenicol/kg BW | | | |
| Formulation A | 5.67 | 3.22 | 163.12 |
| Formulation F | 4.33 | 4.03 | 191.83 |
| Formulation E | 4.17 | 4.39 | 167.53 |
| Reference prior art formulation | 3.83 | 4.05 | 209.64 |
| Intramuscular treatment at a dose of 2 × 20 mg florfenicol/kg BW | | | |
| Formulation A | 6 | 2.03 | 100.16 |
| Formulation F | 4 | 3.02 | 111.01 |
| Reference prior art formulation | 3 | 2.95 | 91.38 |

The invention claimed is:

1. An injectable composition for the treatment of microbial infection in an animal, wherein the composition comprises florfenicol in a solvent system; and the solvent system comprises diethyleneglycol monoethyl ether and a pyrrolidone solvent selected from the group consisting of 2-pyrrolidone and N-methyl-2-pyrrolidone, wherein said composition has a room temperature viscosity of 43 mPa·s or less.

2. The composition according to claim 1, wherein the florfenicol is present at a concentration of from 30% to 45% w/v.

3. The composition according to claim 1, wherein the pyrrolidone solvent is N-methyl-2-pyrrolidone.

4. The composition according to claim 1, wherein the ratio of the amount of pyrrolidone solvent to florfenicol is from 0.6 to 1.1.

5. The composition according to claim 1, wherein the composition comprises from 1 to 89% v/v of diethyleneglycol monoethyl ether and from 1 to 89% w/v of the pyrrolidone solvent.

6. The composition according to claim 1, wherein the composition consists essentially of the following ingredients in the following proportions:

| Florfenicol | 45 g |
|---|---|
| N-methyl-2-pyrrolidone | 35 g |
| Diethylene glycol monoethylether | enough to make total volume = 100 ml. |

7. The composition according to claim 1, wherein the composition consists essentially of the following ingredients in the following proportions:

| Florfenicol | 45 g |
|---|---|
| N-methyl-2-pyrrolidone | 30 g |
| Diethylene glycol monoethylether | enough to make total volume = 100 ml. |

8. The composition according to claim 1, wherein the florfenicol is present at a concentration of from 30% to 45% w/v.

9. An injectable composition for the treatment of microbial infection in an animal, wherein the composition consists essentially of florfenicol in a solvent system; and the solvent system comprises diethyleneglycol monoethyl ether and a pyrrolidone solvent selected from the group consisting of 2-pyrrolidone and N-methyl-2-pyrrolidone, wherein said composition has a room temperature viscosity of 43 mPa·s or less.

* * * * *